(12) United States Patent
Ahn et al.

(10) Patent No.: US 8,946,096 B2
(45) Date of Patent: Feb. 3, 2015

(54) GROUP IV-B ORGANOMETALLIC COMPOUND, AND METHOD FOR PREPARING SAME

(75) Inventors: Dae-jun Ahn, Yongin-Si (KR); Hyun-chang Kim, Suwon-Si (KR)

(73) Assignee: Mecharonics Co. Ltd., Gyeonggi-Do (KR)

( * ) Notice: Subject to any disclaimer, the term of this patent is extended or adjusted under 35 U.S.C. 154(b) by 0 days.

(21) Appl. No.: 14/001,957

(22) PCT Filed: Mar. 2, 2012

(86) PCT No.: PCT/KR2012/001566
§ 371 (c)(1),
(2), (4) Date: Aug. 28, 2013

(87) PCT Pub. No.: WO2012/124913
PCT Pub. Date: Sep. 20, 2012

(65) Prior Publication Data
US 2013/0337659 A1 Dec. 19, 2013

(30) Foreign Application Priority Data

Mar. 15, 2011 (KR) .................. 10-2011-0022615
Feb. 8, 2012 (KR) .................. 10-2012-0012738

(51) Int. Cl.
*H01L 21/02* (2006.01)
*C23C 16/18* (2006.01)
*C23C 16/40* (2006.01)
*C07F 17/00* (2006.01)

(52) U.S. Cl.
CPC .......... *H01L 21/02189* (2013.01); *C23C 16/18* (2013.01); *C23C 16/405* (2013.01); *C07F 17/00* (2013.01); *H01L 21/02181* (2013.01); *H01L 21/02186* (2013.01); *H01L 21/02205* (2013.01); *H01L 21/0228* (2013.01)
USPC .......... 438/785; 556/51; 106/285; 106/287.19

(58) Field of Classification Search
CPC ....... C23C 16/18; C23C 16/405; C07F 17/00; H01L 21/02189
USPC ................. 556/52; 438/785; 106/285, 287.19
See application file for complete search history.

(56) References Cited

U.S. PATENT DOCUMENTS 5,026,798 A 6/1991 Canich
2003/0191334 A1 10/2003 Schottek et al.

FOREIGN PATENT DOCUMENTS

| EP | 0416815 A2 | 3/1991 |
|---|---|---|
| JP | H08-198910 A | 8/1996 |
| KR | 10-2007-0121281 | 12/2007 |
| KR | 10-2010-0016477 | 2/2010 |
| KR | 10-2010-0072021 | 6/2010 |
| WO | 2007/140813 A1 | 12/2007 |
| WO | 2008/128141 A2 | 10/2008 |
| WO | 2009/036046 A1 | 3/2009 |

OTHER PUBLICATIONS

Chirinos et al., Macromol. Chem. Phys., vol. 201, No. 17, pp. 2581-2585 (2000).*
Hughes et al., Organometallics, vol. 12, No. 5, pp. 1936-1945 (1993).*
D.M. Haussmann et al., "Atomic Layer Deposition of Hafnium and Zirconium Oxides Using Matel Amide Precursors", Chem. Mater. 2002, 14, pp. 4350-4358.
Jaakko Niinisto et al., "Novel mixed alkylamido-cyclopentadienyl precursors for ALD of ZrO2 thin firms", Journal of Materials Chemistry 2008, 18, pp. 5243-5247.
Marsh, Sarah Margaret Beatrice (1997) New amine-substituted cyclopentadienyl and indenyl ligands, Durham theses, Durham University. Available at Durham E-Theses Online: http://etheses.dur.ac.uk/5012/.
Prof. dr. B.L. Feringa et al., "Carbon-Bridged Cyclopentadienyl Amido Group 4 Metal Complexes", Chapter 5, pp. 119-151, Apr. 23, 1999.

* cited by examiner

Primary Examiner — Porfirio Nazario Gonzalez
(74) Attorney, Agent, or Firm — Jacobson Holman, PLLC.

(57) ABSTRACT

The present invention relates to novel 4B group metalorganic compounds represented by following formula I and the preparation thereof. Specifically, the present invention relates to a thermally and chemically stable 4B group organo-metallic compound utilized in chemical vapor deposition (CVD) or atomic layer deposition (ALD), and the preparation thereof. A 4B group metalorganic compound prepared according to the present invention volatiles easily and is stable at high temperature, and can be used effectively in manufacturing 4B group metal oxide thin films.

formula I

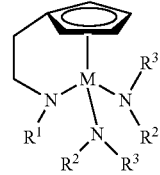

wherein
M represents Ti, Zr or Hf,
$R^1$ represents $C_1$~$C_4$ alkyl,
$R^2$ and $R^3$ represent independently $C_1$~$C_6$ alkyl.

19 Claims, 7 Drawing Sheets

GROUP IV-B ORGANOMETALLIC COMPOUND, AND METHOD FOR PREPARING SAME

This is a national stage of PCT/KR12/001566 filed Mar. 2, 2012 and published in Korean, which has a priority of Korean no. 10-2011-0022615 filed Mar. 15, 2011, and Korean no. 10-2012-0012738 filed Feb. 8, 2012, hereby incorporated by reference.

TECHNICAL FIELD

The present invention relates to the novel 4B group metalorganic compounds and their synthesis, and to a method for chemical vapor deposition (CVD), especially for atomic layer deposition (ALD) using the novel 4B group metalorganic compounds.

BACKGROUND

As a result of increase of components per chip, the structure of memory or non-memory semiconductor devices has been complicated, and the importance of step coverage has been increased when depositing thin film in great variety on the substrate.

In a metal oxide thin film manufacturing process such as chemical vapor deposition (CVD) or atomic layer deposition (ALD), the metalorganic compounds demand specific properties, such as high volatile nature, high temperature difference between evaporation and decomposition, low toxicity, chemical stability, heat stability, easiness of chemical synthesis and thermolysis.

Further, the metalorganic compounds should not be voluntarily decomposed nor have side reaction with other materials during the evaporation and conveying processes thereof. Particularly, in order to obtain good multi-components thin films, ratio of metal components introduced can be easily controlled and decomposition behaviors of metal precursors at deposition temperature should be similar each other.

As thin films for manufacturing semiconductors, metal nitrides, metal oxides, metal silicates or metals, etc. are usually used. Examples of representative metal nitrides are titanium nitride (TiN), tantalum nitride (TaN) and zirconium nitride (ZrN). The thin film of metal nitrides is effected as a diffusion barrier between a silicon layer of doped semiconductor and a wiring layer connecting semiconductor layers such as aluminum or copper.

The thin film of metal nitrides is effected as an adhesion layer when tungsten thin films are deposited on the substrates.

Examples of representative metal silicates for manufacturing thin films are titanium silicates and tantalum silicates. The thin film of metal silicates is effected as an adhesion layer between silicon substrates and electrodes/wiring materials/diffusion barriers. When depositing metal thin film on silicon layers, a metal silicate such as titanium silicates or tantalum silicates is used to improve adhesion.

It is known that metal oxides such as alumina ($Al_2O_3$), titania ($TiO_2$) or tantalia ($Ta_2O_5$) etc., are used for capacitors of semiconductor devices, and have dielectric constants ($\in$) higher than those of silicates ($SiO_2$), and these materials are utilized in manufacturing memory semiconductors having large scale integration and/or high capacity.

As described above, the selection of precursor is the most important requirement in order for deposited thin films to have good properties. For example, when titanium nitrates (TiN) are deposited on substrates using titanium chlorides ($TiCl_4$), this precursor has the following problems despite of good economic feasibility thereof.

Chlorine atoms presented in precursors are introduced into the deposited titanium nitride thin film, and induce corrosions of aluminum wiring materials. In addition, as deposition temperature is high (around 600° C.), this process cannot be adopted when wiring materials are aluminums having low melting point. Further, during deposition processes, non-volatile materials, such as titanium chloride ammonium complexes ($TiCl_4:NH_3)_x$ and ammonium chloride salts ($NH_4Cl$) are formed and these materials are accumulated in thin films, the produced semiconductor chips induce critical demerits.

Additionally, tantalum chlorides ($TaCl_5$) or zirconium chlorides ($ZrCl_4$) are used in order to deposit tantalum nitrides (TaN) film or zirconium nitrides (ZrN) film on substrates. However, above chlorides are not easy to use as precursors, since these are solids, which cannot supply a sufficient vapor for deposit processes.

Further, either processes for forming titanium nitride (TiN) films using titanium amides[$Ti(NR_2)_4$:R=$CH_3$ or $C_2H_5$] or processes for forming tantalia ($Ta_2O_3$) films using tantalum ethoxides are developed for dielectric films, these precursors are unstable and dangerous materials.

Zirconia ($ZrO_2$) has higher dielectric constant ($\in$) than that of silicon dioxide (SiO2). And when it is applied in capacitors of semiconductor devices, high integrated and high capacity memory semiconductors can be obtained.

As zirconium compounds which are most frequently applied in metaloganic chemical vapor deposition (MOCVD) and atomic layer deposition (ALD) processes, TEMAZ[$Zr(NMeEt)_4$: (tetrakis-ethylmethylamidozirconiums]can be exemplified (D. M. Hausmann et. al., Chem. Mater., 2002. 14, 4350).

TEMAZ is liquid at room temperature and has high vapor pressure, however it has low thermal stability and causes low step coverage and capacitor leakage. Accordingly, TEMAZ is to have the limits in adaptability either MOCVD process or ALD process for next generation semiconductor devices.

In ALD process, CpTDMAZ [cyclopentadienyltrisdimethylamidozirconium; $CpZr(NMe_2)_3$] is known as substitutive one of TEMAZ (Jaakko Niinisto et al. J. Mater. Chem. 2008, 18, 5243)

Paper describes that CpTDMAZ is liquid at room temperature and has high vapor pressure, and is more stable at high deposition temperature in comparison with TEMAZ. However, CpTDMAZ has demerits to produce undesirable by-products when it is applied in ALD process.

TDMAT [tetrakis-dimethylamidotitanium; $Ti(NMe_2)_4$] can be exemplified as a titanium compound which is most frequently applied in either MOCVD process or ALD process. And TEMAH [tetrakis-ethylmethylamidohafnium; $Hf(NEtMe)_4$] can be exemplified as the hafnium compound. However, these compounds also cannot be used in next generation semiconductor devices due to same reasons with TEMAZ as described in above. Any substitute compound of TDMAT or TEMAH, which can be applied in ALD process, is not yet reported.

Atomic layer deposition (ALD) is a known thin film deposition method.

ALD comprises the steps of (1) vaporizing metalorganic compounds by heating a vessel containing them to around 100° C.~110° C. for long hours and (2) transporting them to substrates as gaseous phase to deposit on substrate. However, during vaporizing and transporting steps, CpTDMAZ, TDMAT or TEMAH provides multi-component compounds via voluntarily intermolecular reactions. Accordingly when CpTDMAZ, TDMAT or TEMAH is applied, thickness control of thin film is difficult and good quality films cannot be obtained. As an alternative, liquid injection ALD is known, in which liquid compositions comprising metalorganic precursor compounds and their suitable stabilizing solvent such as hydrocarbons, ethers and amines are used as precursors.

Precursors forming 4B group metal oxides in CVD or ALD process are described below. But structures of these precursors are different those of novel 4B group metalorganic precursors of the present invention and their chemical properties are also different each other.

WO 2007/140813A1 (Dec. 13, 2007; Air LiquideSociete)
KR 2007/0121281A1 (Dec. 27, 2007; DNF)
KR 2010/0016477A1 (Feb. 12, 2010; Advanced Technology Materials)
D. M. Haussmann et. al., Chem. Mater., 2002, 14, 4350
Jaakko Niinisto et. al., J. Mater. Chem., 2008, 18, 5243

DETAILED DESCRIPTION OF THE INVENTION

Technical Subject

The present invention is intended to solve the problems in the prior-art described above. Namely, the present invention provides metalorganic compounds, of which thermal stability and step coverage are much better than those of CpTDMAZ, TDMAT or TEMAH. The present invention also provides novel metalorganic compounds (novel 4B group oxide precursors) which do not decompose after long time storage at high temperature (please refer to drawings attached).

The present invention aims to provides metalorganic compounds having high thermal stability and high volatility so that good 4B group metal oxide thin films can be obtained in CVD or ALD process, preparation thereof and a thin film forming method using them.

Subject Solving Method

The invention will be described in detail in the following.
The present invention provides novel 4B group oxide precursors represented by following Formula I:

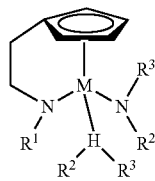

Formula I wherein
M represents Ti, Zr or Hf;
$R^1$ represents $C_1\text{~}C_4$ alkyl;
$R^2$ and $R^3$ represent independently $C_1\text{~}C_6$ alkyl.

Preferred compounds represented by above Formula I are those in which $R^1$, $R^2$, and $R^3$ represent independently methyl, ethyl or propyl. More preferred compounds represented by above Formula I are those in which $R^1$, $R^2$, and $R^3$ represent independently methyl or ethyl. Further preferred compounds represented by above Formula I are those in which all of $R^1$, $R^2$, and $R^3$ represent methyl. Most preferred compounds represented by above Formula I are those in which both of $R^1$ and $R^2$ represent methyl and $R^3$ represents ethyl.

The representative compounds of above Formula I are listed in the following.

Zr(CpCH$_2$CH$_2$NMe)(NMe$_2$)$_2$, Zr(CpCH$_2$CH$_2$NMe)(NMeEt)$_2$, Zr(CpCH$_2$CH$_2$NMe)(NEt$_2$)$_2$, Zr(CpCH$_2$CH$_2$NMe)(NMe$^i$Pr)$_2$, Zr(CpCH$_2$CH$_2$NMe)(NEt$^i$Pr)$_2$, Zr(CpCH$_2$CH$_2$NMe)(N$^i$Pr)$_2$, Zr(CpCH$_2$CH$_2$NMe)(NMe$''$Pr)$_2$, Zr(CpCH$_2$CH$_2$NMe)(NEt$''$Pr)$_2$, Zr(CpCH$_2$CH$_2$NMe)(N$''$Pr)$_2$, Zr(CpCH$_2$CH$_2$NEt)(NMe$_2$)$_2$, Zr(CpCH$_2$CH$_2$NEt)(NMeEt)$_2$, Zr(CpCH$_2$CH$_2$NEt)(NEt$_2$)$_2$, Zr(CpCH$_2$CH$_2$NEt)(NMe$^i$Pr)$_2$, Zr(CpCH$_2$CH$_2$NEt)(NEt$^i$Pr)$_2$, Zr(CpCH$_2$CH$_2$NEt)(N$^i$Pr)$_2$, Zr(CpCH$_2$CH$_2$NEt)(NMe$^i$Pr)$_2$, Zr(CpCH$_2$CH$_2$NEt)(NEt$^i$Pr)$_2$, Zr(CpCH$_2$CH$_2$NEt)(N$''$Pr)$_2$, Zr(CpCH$_2$CH$_2$N$^i$Pr)(NMe$_2$)$_2$, Zr(CpCH$_2$CH$_2$N$^i$Pr)(NMeEt)$_2$, Zr(CpCH$_2$CH$_2$N$^i$Pr)(NEt$_2$)$_2$, Zr(CpCH$_2$CH$_2$N$^i$Pr)(NMe$^i$Pr)$_2$, Zr(CpCH$_2$CH$_2$N$^i$Pr)(NEt$^i$Pr)$_2$, Zr(CpCH$_2$CH$_2$N$^i$Pr)(N$^i$Pr)$_2$, Zr(CpCH$_2$CH$_2$N$^i$Pr)(NMe$''$Pr)$_2$, Zr(CpCH$_2$CH$_2$N$^i$Pr)(NEt$''$Pr)$_2$, Zr(CpCH$_2$CH$_2$N$^i$Pr)(N$''$Pr)$_2$, Zr(CpCH$_2$CH$_2$N$''$Pr)(NMe$_2$)$_2$, Zr(CpCH$_2$CH$_2$N$''$Pr)(NMeEt)$_2$, Zr(CpCH$_2$CH$_2$N$''$Pr)(NEt$_2$)$_2$, Zr(CpCH$_2$CH$_2$N$''$Pr)(NMe$^i$Pr)$_2$, Zr(CpCH$_2$CH$_2$N$''$Pr)(NEt$^i$Pr)$_2$, Zr(CpCH$_2$CH$_2$N$''$Pr)(N$^i$Pr)$_2$, Zr(CpCH$_2$CH$_2$N$''$Pr)(NMe$''$Pr)$_2$, Zr(CpCH$_2$CH$_2$N$''$Pr)(NEt$''$Pr)$_2$, Zr(CpCH$_2$CH$_2$N$''$Pr)(N$''$Pr)$_2$ Ti(CpCH$_2$CH$_2$NMe)(NMe$_2$)$_2$, Ti(CpCH$_2$CH$_2$NMe)(NMeEt)$_2$, Ti(CpCH$_2$CH$_2$NMe)(NEt$_2$)$_2$, Ti(CpCH$_2$CH$_2$NMe)(NMe$^i$Pr)$_2$, Ti(CpCH$_2$CH$_2$NMe)(NEt$^i$Pr)$_2$, Ti(CpCH$_2$CH$_2$NMe)(N$^i$Pr)$_2$, Ti(CpCH$_2$CH$_2$NMe)(NMe$''$Pr)$_2$, Ti(CpCH$_2$CH$_2$NMe)(NEt$''$Pr)$_2$, Ti(CpCH$_2$CH$_2$NMe)(N$''$Pr)$_2$, Ti(CpCH$_2$CH$_2$NEt)(NMe$_2$)$_2$, Ti(CpCH$_2$CH$_2$NEt)(NMeEt)$_2$, Ti(CpCH$_2$CH$_2$NEt)(NEt$_2$)$_2$, Ti(CpCH$_2$CH$_2$NEt)(NMe$^i$Pr)$_2$, Ti(CpCH$_2$CH$_2$NEt)(NEt$^i$Pr)$_2$, Ti(CpCH$_2$CH$_2$NEt)(N$^i$Pr)$_2$, Ti(CpCH$_2$CH$_2$NEt)(NMe$''$Pr)$_2$, Ti(CpCH$_2$CH$_2$NEt)(NEt$''$Pr)$_2$, Ti(CpCH$_2$CH$_2$NEt)(N$''$Pr)$_2$, Ti(CpCH$_2$CH$_2$N$^i$Pr)(NMe$_2$)$_2$, Ti(CpCH$_2$CH$_2$N$^i$Pr)(NMeEt)$_2$, Ti(CpCH$_2$CH$_2$N$^i$Pr)(NEt$_2$)$_2$, Ti(CpCH$_2$CH$_2$N$^i$Pr)(NMe$^i$Pr)$_2$, Ti(CpCH$_2$CH$_2$N$^i$Pr)(NEt$^i$Pr)$_2$, Ti(CpCH$_2$CH$_2$N$^i$Pr)(N$^i$Pr)$_2$, Ti(CpCH$_2$CH$_2$N$^i$Pr)(NMe$''$Pr)$_2$, Ti(CpCH$_2$CH$_2$N$^i$Pr)(NEt$''$Pr)$_2$, Ti(CpCH$_2$CH$_2$N$^i$Pr)(N$''$Pr)$_2$, Ti(CpCH$_2$CH$_2$N$''$Pr)(NMe$_2$)$_2$, Ti(CpCH$_2$CH$_2$N$''$Pr)(NMeEt)$_2$, Ti(CpCH$_2$CH$_2$N$''$Pr)(NEt$_2$)$_2$, Ti(CpCH$_2$CH$_2$N$''$Pr)(NMe$^i$Pr)$_2$, Ti(CpCH$_2$CH$_2$N$''$Pr)(NEt$^i$Pr)$_2$, Ti(CpCH$_2$CH$_2$N$''$Pr)(N$^i$Pr)$_2$, Ti(CpCH$_2$CH$_2$N$''$Pr)(NMe$''$Pr)$_2$, Ti(CpCH$_2$CH$_2$N$''$Pr)(NEt$''$Pr)$_2$, Ti(CpCH$_2$CH$_2$N$''$Pr)(N$''$Pr)$_2$ Hf(CpCH$_2$CH$_2$NMe)(NMe$_2$)$_2$, Hf(CpCH$_2$CH$_2$NMe)(NMeEt)$_2$, Hf(CpCH$_2$CH$_2$NMe)(NEt$_2$)$_2$, Hf(CpCH$_2$CH$_2$NMe)(NMe$^i$Pr)$_2$, Hf(CpCH$_2$CH$_2$NMe)(NEt$^i$Pr)$_2$, Hf(CpCH$_2$CH$_2$NMe)(N$^i$Pr)$_2$, Hf(CpCH$_2$CH$_2$NMe)(NMe$''$Pr)$_2$, Hf(CpCH$_2$CH$_2$NMe)(NEt$''$Pr)$_2$, Hf(CpCH$_2$CH$_2$NMe)(N$''$Pr)$_2$, Hf(CpCH$_2$CH$_2$NEt)(NMe$_2$)$_2$, Hf(CpCH$_2$CH$_2$NEt)(NMeEt)$_2$, Hf(CpCH$_2$CH$_2$NEt)(NEt$_2$)$_2$, Hf(CpCH$_2$CH$_2$NEt)(NMe$^i$Pr)$_2$, Hf(CpCH$_2$CH$_2$NEt)(NEt$^i$Pr)$_2$, Hf(CpCH$_2$CH$_2$NEt)(N$^i$Pr)$_2$, Hf(CpCH$_2$CH$_2$NEt)(NMe$''$Pr)$_2$, Hf(CpCH$_2$CH$_2$NEt)(NEt$''$Pr)$_2$, Hf(CpCH$_2$CH$_2$NEt)(N$''$Pr)$_2$, Hf(CpCH$_2$CH$_2$N$^i$Pr)(NMe$_2$)$_2$, Hf(CpCH$_2$CH$_2$N$^i$Pr)(NMeEt)$_2$, Hf(CpCH$_2$CH$_2$N$^i$Pr)(NEt$_2$)$_2$, Hf(CpCH$_2$CH$_2$N$^i$Pr)(NMe$^i$Pr)$_2$, Hf(CpCH$_2$CH$_2$N$^i$Pr)(NEt$^i$Pr)$_2$, Hf(CpCH$_2$CH$_2$N$^i$Pr)(N$^i$Pr)$_2$, Hf(CpCH$_2$CH$_2$N$^i$Pr)(NMe$''$Pr)$_2$, Hf(CpCH$_2$CH$_2$N$^i$Pr)(NEt$''$Pr)$_2$, Hf(CpCH$_2$CH$_2$N$^i$Pr)(N$''$Pr)$_2$, Hf(CpCH$_2$CH$_2$N$''$Pr)(NMe$_2$)$_2$, Hf(CpCH$_2$CH$_2$N$''$Pr)(NMeEt)$_2$, Hf(CpCH$_2$CH$_2$N$''$Pr)(NEt$_2$)$_2$, Hf(CpCH$_2$CH$_2$N$''$Pr)(NMe$^i$Pr)$_2$, Hf(CpCH$_2$CH$_2$N$''$Pr)(NEt$^i$Pr)$_2$, Hf(CpCH$_2$CH$_2$N$''$Pr)(N$^i$Pr)$_2$, Hf(CpCH$_2$CH$_2$N$''$Pr)(NMe$''$Pr)$_2$, Hf(CpCH$_2$CH$_2$N$''$Pr)(NEt$''$Pr)$_2$, Hf(CpCH$_2$CH$_2$N$''$Pr)(N$''$Pr)$_2$

Wherein $^iPr$ and $^nPr$ each represents isopropyl and normal propyl.

4B group compounds of Formula I can be easily prepared according to following reaction schemes 1 to 3. Reaction solvents can be used in the synthesis of above 4B group compounds. Examples of the reaction solvents are non-polar solvents such as hexane, pentane, heptane, benzene and toluene, and polar solvents such as diethyl ether, petroleum ether, tetrahydrofuran and 1,2-dimethoxyethane.

4B group compounds of Formula I according to the present invention can be prepared by reacting a product (a compound of Formula II) of reaction scheme 1 with a compound of Formula III.

Reaction Scheme 1

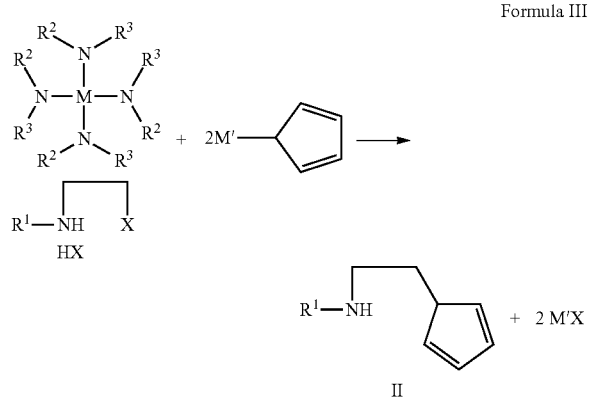

In above reaction scheme 1 and formula III, M represents Ti, Zr or Hf; $R^1$, $R^2$ and $R^3$ are as defined in above Formula I; X represents Cl, Br or I; and M' represents Li, Na or K.

Halogenethylalkylaminehalogenacid salts used in reaction scheme 1, are easily prepared according to the descriptions in Organic Syntheses Wiley: New York, 1943; Collective volume 4, p 333. A compound of formula II is prepared by introducing a freshly synthesized metalcyclopentadienyl to above halogenethylalkylaminehalogenacid salt and refluxing them to complete the reaction. After filtering off the solid salt thus obtained and removing the solvent under reduced pressure (via vacuum distillation), the products of reaction scheme 1 (compounds of formula II) are prepared.

Reaction Scheme 2

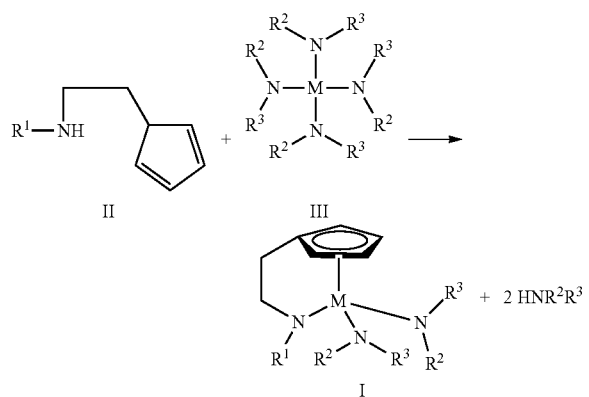

In above reaction scheme 2, M represents Ti, Zr or Hf; and $R^1$, $R^2$ and $R^3$ are as defined in above Formula I.

The 4B group compound of formula I are prepared in high yield by reacting the compound of formula II with the metallic compound of formula III. After cooling a tetrakis(dialkylamido)4-B group metal (IV) (formula III) to a low temperature and adding hereto a cyclopentadienylethylalkylamine (formula II), the reaction solution is stirred for one hour at room temperature to complete the reaction. Then the solvent is removed under reduced pressure and the liquid remained is distilled under vacuum pressure to obtain the subject compound in high yield.

As depicted in reaction scheme 3 below, the 4B group compounds of formula I according to the present invention are also prepared by reacting the compound of formula IV (M'NR²R³) with the compound of formula V. After charging the cyclopentadienyl(ethylalkylamido) 4B group metal (IV) dihalide (formula V) into a reactor and cooling it to −20° C., a metal dialkylamide (M'NR²R³) (IV) suspended in n-hexane is slowly added through a cannula and the reaction mixture is stirred at room temperature for 15 hours to complete reaction. After the mixture is allowed to stand at room temperature for a sufficient time, the supernatant is transferred to another flask through a canula. Then the solvent is removed under reduced pressure and the remained liquid is distilled under vacuum pressure to obtain the compound of formula I Reaction Scheme 3

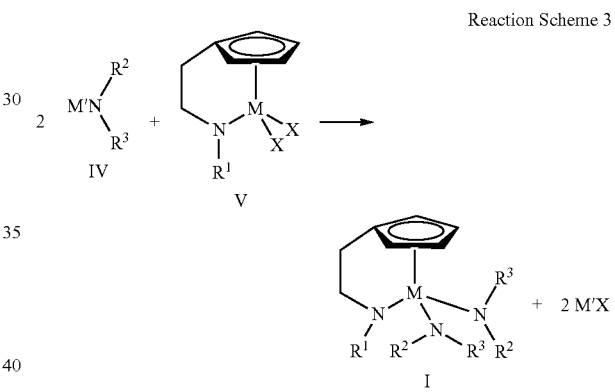

In above reaction scheme 3, M represents Ti, Zr or Hf; $R^1$, $R^2$ and $R^3$ are as defined in above Formula I; X represents Cl, Br or I; and M' represents Li, Na or K.

4B group metalorganic compounds of Formula I are deposited onto the substrate by a conventional deposition process. For deposition of the 4B group metalorganic compound of Formula I, any of known deposition processes can be used, but metal organic chemical vapor deposition (MOCVD) or atomic layer deposition (ALD) is preferred and it is applied onto any of known substrates, but silicon substrates or metal, ceramic, plastic structure substrates are preferred.

The 4B group metalorganic compounds of Formula I are usually utilized alone or as the mixture of more than two. For stabilization of the compounds, a composition comprising of 0.1 wt % 99.9 wt %, preferably 1 wt %~99 wt % of the 4B group metalorganic compound and remainder of one or more organic compounds selected from the group of saturated or unsaturated hydrocarbons, ethers (including cyclic ethers), esters, alcohols, amines (including cyclic amines), sulfides (including cyclic sulfides), phosphines, beta-diketones and beta-ketoesters, etc. can be used.

Organic compounds added to above composition are not limited, if they stabilize 4B group metalorganic compounds of Formula I. Examples of saturated or unsaturated hydrocarbons are aliphatic hydrocarbons such as propane, butane, pentane, hexane, heptane, octane, ethene, propene, butene, pentene, hexene, heptene, octene, ethyne, propyne, butyne, pentyne, hexyne, heptyne, octyne; cyclic hydrocarbons such as cyclopropane, cyclobutane, cyclopentane, cyclohexane, methylcyclohexane, dimethylcyclohexane, trimethylcyclohexane, ethylcyclohexane, diethylcyclohexane, decahydronaphthalene, bicycloheptane, hexahydroindene cyclohexane, cyclooctane, etc.; aromatic hydrocarbons such as benzene, toluene, xylene, mesitylene etc.; or mixtures thereof, but they are not limited thereto. Examples of ethers (including cyclic ethers) are tetrahydrofuran, diethylether, methyl t-butylether or mixtures thereof, but they are not limited thereto. Examples of esters are methyl acetate, ethyl acetate, butyl acetate, butylcellosolve acetate, propyleneglycolmonomethylether acetate, diethyleneglycolmonoethylether acetate or mixtures thereof, but they are not limited thereto. Examples of alcohols are methanol, ethanol, propanol, butanol or mixtures thereof, but they are not limited thereto. Examples of amides (including cyclic amides) are N,N-dimethyl formamide, N,N-dimethyl acetamide, N-methyl pyrrolidone or mixtures thereof, but they are not limited thereto. Examples of sulphoxides (including cyclic sulphoxides) are dimethyl sulphoxide, methylethylsulphoxide or mixtures thereof, but they are not limited thereto. An example of phosphine is triphenylphosphine, tricyclohexylphosphine or a mixture thereof, but it is not limited thereto. Examples of beta-diketones are dimethyl beta-diketone, methylethylbeta-diketone, methylisobutylbeta-diketone or mixtures thereof, but they are not limited thereto. Examples of beta-ketoesters are methylacetoacetate, ethylacetoacetate or mixtures thereof, but they are not limited thereto.

Depositing temperature for forming thin films which contain the 4B group metalorganic compound of Formula I, is 100~1000° C., preferably 200~500° C., more preferably 250~450° C., and in the depositing step any one of heat energy, light energy, plasma or bias voltage is used as an energy source.

A method for delivering 4B group metalorganic compounds of the Formula I onto substrates, is one selected from float method, bubbling method, vapor phase mass flow controller (MFC) method, direct liquid injection (DLI) method or liquid transferring method using precursor compound-organic solvent solution.

Carrier gas or dilution gas for delivering the 4B group metalorganic compounds of Formula I onto substrates is any one selected from argon, nitrogen, helium, hydrogen and mixtures thereof. As reaction gas, any one selected from water vapor ($H_2O$), oxygen ($O_2$), ozone ($O_3$), hydrogen peroxide ($H_2O_2$), ammonia gas ($NH_3$), hydrazine ($NH_2NH_2$) and mixtures thereof can be used.

A thin film deposited on substrates according to the present invention is any one of 4B group metal oxide ($MO_2$) film, 4B group metal nitride (MN) film, 4B group metal carbide (MC) film or 4B group metal carbon nitrides (MCN) film; or metal oxides composite film containing 4B group metal oxide ($MO_2$) film and more than one film selected from the group of oxide film of Sc, Y, La, Ac, oxide film of V, Nb, Ta, oxide film of AL, Ga, In, and oxide film of Si, Ge, Sn, Pb; or metal nitrides composite film containing 4B group metal nitride (MN) film and more than one film selected from the group of nitride film of Sc, Y, La, Ac, nitride film of V, Nb, Ta, nitride film of AL, Ga, In, and nitride film of Si, Ge, Sn, Pb; or metal carbides composite film containing 4-B group metal carbide (MC) film and more than one film selected from the group of carbide film of Sc, Y, La, Ac, carbide film of V, Nb, Ta, carbide film of AL, Ga, In, and carbide film of Si, Ge, Sn, Pb; or metal carbon nitrides composite film containing 4B group metal carbon nitride (MCN) film and more than one film selected from the group of carbon nitride film of Sc, Y, La, Ac, carbon nitride film of V, Nb, Ta, carbon nitride film of AL, Ga, In, and carbon nitride film of Si, Ge, Sn, Pb.

A method for forming thin films using atomic layer deposition (ALD), according to the present invention comprises steps of:

(1) Carrying a substrate into the reaction chamber and heating it to sintering temperature thereof;
(2) Introducing first purging gas into the chamber (first purging step);
(3) Supplying a 4B group compound into the chamber to form an atomic layer on the substrate;
(4) Supplying a reaction gas into the chamber to react with the atomic layer; and
(5) Releasing off by-products and un-reacted materials of the 4B group compound from above chamber using second purging gas (second purging step). In first and second purging steps, more than one selected from the group of He, $H_2$, $N_2$, Ar, and $NH_3$ are introduced into the chamber and vacuum pumps may be used when gases in the chamber are released off.

The metalorganic compounds of Formula I according to the present invention have some ligands bonded to center metal atom. Among them, cyclopentadienyl one connected to alkylamide ligand is forming strong σ-bond and π-bond with the center metal atom. Thus, metalorganic compounds of the present invention do not decompose for a long-time heating, namely has high heat stability. Further, metalorganic compounds of the present invention have high vapor pressure since the two dialkylamino ligands are bonded to the center metal atom.

Temperatures at which weight of test compounds are reduced to 50 wt % ($T_{1/2}$° C.) are determined from TGA graph of FIG. 1 and listed in Table 1 below. Known TEMAZ and CpTDMAZ, and compounds prepared in examples 1 and 2 are tested.

TABLE 1

| compounds | TEMAZ | CpTDMAZ | Example 1 | Example 2 |
|---|---|---|---|---|
| $T_{1/2}$° C. | 164° C. | 176° C. | 195° C. | 202° C. |

From table 1, $T_{1/2}$° C. of compounds prepared according to example 1 and example 2 of the present invention are each 195° C. and 202° C. However, $T_{1/2}$° C. of known TEMAZ and CpTDMAZ are each 164° C. and 176° C.

Accordingly, the 4B group metalorganic compounds of Formula I according to the present invention, have extraordinarily higher $T_{1/2}$° C. compared to those of known TEMAZ and CpTDMAZ, which means that heat stability of the compounds according to the present invention is highly improved.

Temperatures at which weight of test compounds are reduced to 50 wt % ($T_{1/2}$° C.) are determined from TGA graph of FIG. 2 and FIG. 3 and listed in Table 2 below. Known TDMAT [Ti(NMe$_2$)$_4$; tetrakis(dimethylamido)titanium] and TEMAH [Hf(NEtMe)$_4$; tetrakis(ethylmethylamido) hafnium] and compounds prepared in examples 5 and 7 are tested.

TABLE 2

| compounds | TDMAT | Example 5 | TEMAH | Example 7 |
|---|---|---|---|---|
| $T_{1/2}$° C. | 79° C. | 202° C. | 168° C. | 181° C. |

From table 2, $T_{1/2}°$ C. of compound prepared in example 5 of the present invention, namely cyclopentadienyl(ethylmethylamido)titanium(IV) di(dimethylamide) [(CpCH$_2$CH$_2$NCH$_3$)Ti(NMe$_2$)$_2$] is 202° C. However, $T_{1/2}°$ C. of known TDMAT [Ti(NMe$_2$)$_4$; tetrakis(dimethylamido) titanium] is 79° C. Namely, titanium compound prepared according to the present invention, has extraordinarily higher $T_{1/2}°$ C. compared to that of known TDMAT, which means that heat stability is highly improved.

$T_{1/2}°$ C. of compound prepared in example 7 of the present invention, namely cyclopentadienyl(ethylmethylamido) hafnium(IV)di(ethylmethylamide)[(CpCH$_2$CH$_2$N CH$_3$)Hf(NEtMe)$_2$] is 181° C. However, $T_{1/2}°$ C. of known TEMAH [Hf(NEtMe)$_4$; tetrakis(ethylmethylamido)hafnium] is 168° C. Namely, $T_{1/2}°$ C. of the hafnium compound prepared according to the present invention is more than 10° C. higher than that of TEMAH, which means that heat stability of hafnium compound according to the present invention has improved.

FIGS. 4A, 4B, 5A and 5B are $^1$H nuclear magnetic resonance ($^1$H NMR) graphs, which depict heat stability test results of CpTDMAZ and compound of example 1. Above tests were performed according to test method in example 8.

Specifically, FIG. 4A is $^1$H NMR graph depicting state of CpTDMAZ before heating and FIG. 4B is $^1$H NMR graph depicting state of CpTDMAZ after heating. From FIGS. 4A and 4B, it is found that CpTDMAZ was easily decomposed to produce impurities after heating. However, From FIGS. 5A (compound of example 1 before heating) and 5B (compound of example 1 after heating), it is found that the compound of example 1 has no specific change after heating. Accordingly, it confirms that the heat stability of zirconium compound prepared in example 1 of the present invention has highly improved comparing to that of known CpTDMAZ.

As a result, the novel 4B group oxide precursors of the present invention are preferably utilized as precursors for manufacturing 4B group thin films and all kinds of oxide thin films containing 4B group oxides in semiconductor making processes, especially in metalorganic vapor deposition (MOCVD) or atomic layer deposition (ALD) processes.

Effect of Invention

As precursor compounds of the present invention have high thermal stability and high volatility, they can be utilized for forming complicated thin films required in a next generation semiconductor devices, and can also raise reliability and efficiency of semiconductor manufacturing processes.

INDUSTRIAL APPLICABILITY EXAMPLES

Figure 1:
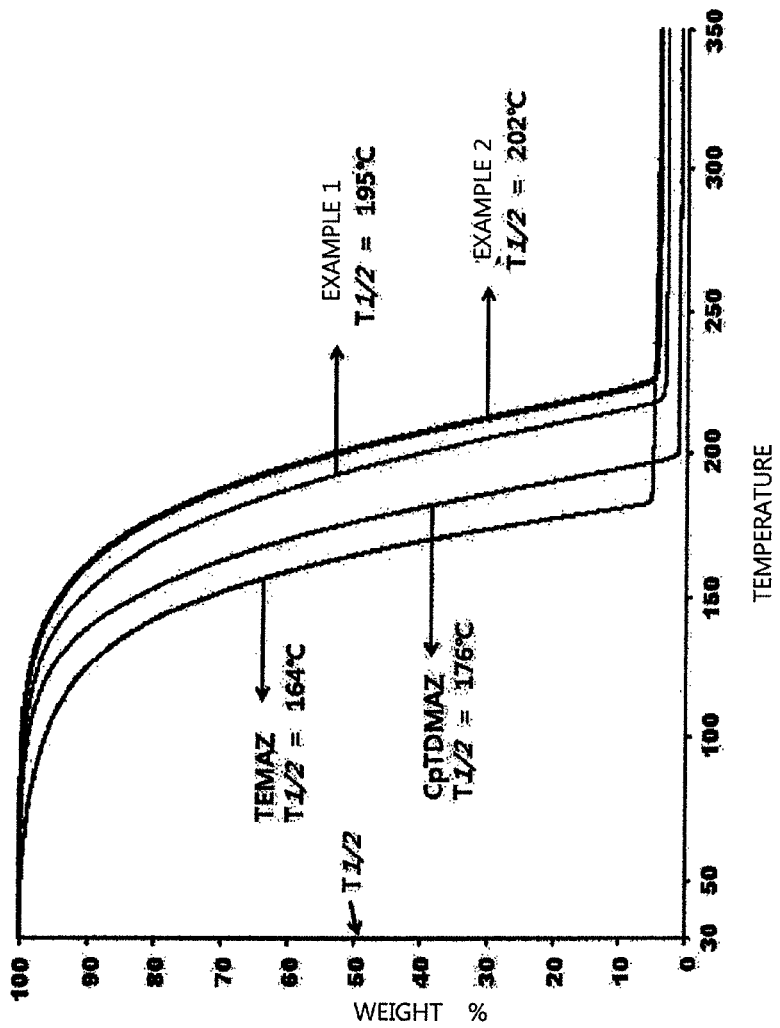
FIG. 1 is thermo-gravimetric-analysis (TGA) graphs of TEMAZ, CpTDMAZ and compounds of examples 1 and 2.
Figure 2:
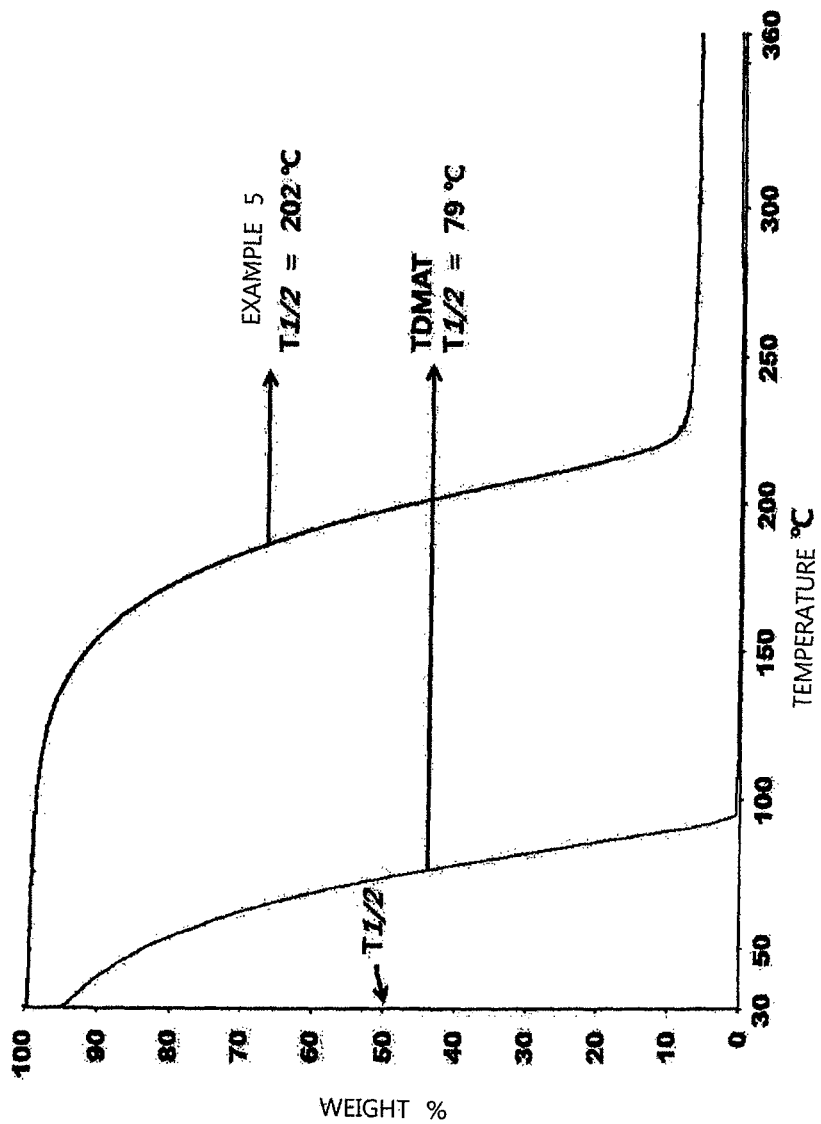
FIG. 2 is TGA graphs of TDMAT and compound of example 5.
Figure 3:
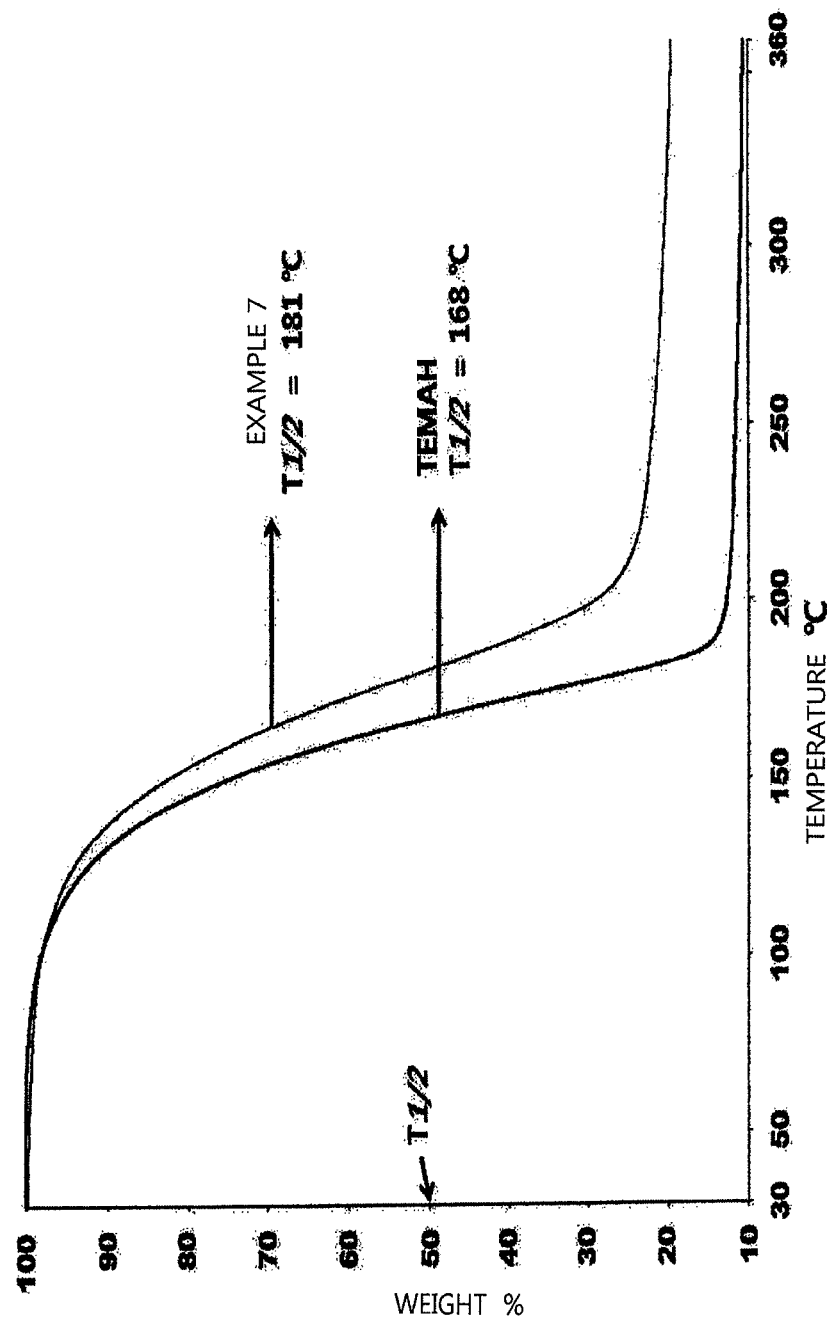
FIG. 3 is TGA graph of TEMAH and compound of example 7.

Following examples are merely illustrative, and do not limit this disclosure in any way.

All manipulations were carried out under inert argon atmospheres using glove box and Schlenk line techniques. Compounds obtained by examples 1~7 were determined by nuclear magnetic resonance analysis (both $^1$H NMR and $^{13}$C NMR).

Example 1

Synthesis of (CpCH$_2$CH$_2$NCH$_3$)Zr(NMe$_2$)$_2$

Step 1:

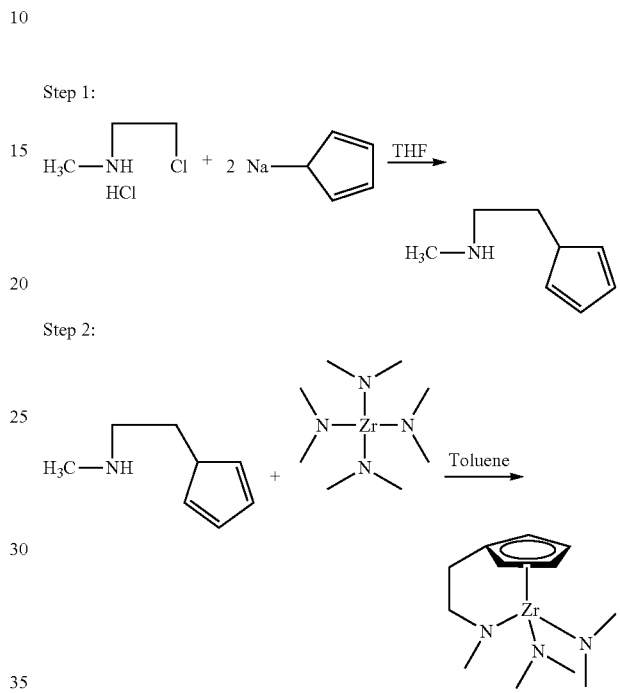

Step 2:

Step 1: A 2-liter Schlenk flask was flame-dried and charged with 500 ml of tetrahydrofuran and 68.2 g (0.524 mol; 1.00 equivalent) of chloroethylmethylamine hydrochloride prepared according to the method which is described in Organic Syntheses: Wiley: New York, 1943; Collective volume 4, p 333. The mixture was stirred and cooled to 0° C. Then 92.3 g (1.048 mol; 2.00 equivalents) of sodium cyclopentadienyl (NaCp) was added over 30 minutes. The reaction mixture was allowed to reach room temperature and refluxed for 4 hours. Reaction was completed by cooling the solution to room temperature. After filtering off solid NaCl obtained, the solvent was completely removed under reduced pressure. The obtained liquid was distilled under reduced pressure (boiling point: 25° C.@0.2 mmHg) yielding 32.3 g of step-1 compound as a transparent liquid in 50% yield.

Step-2: A 250 ml Schlenk flask was flame-dried and charged with 80 ml of toluene and 26.8 g (0.100 mol; 1.00 equivalent) of tetrakis(dimethylamido) zirconium(IV). The mixture was stirred and cooled to −20° C. 12.3 g (0.10 mol; 1.00 equivalents) of cyclopentadienylethylmethylamine synthesized in step-1 was added over 30 minutes. After reaction mixture was stirred at room temperature for one hour, the reaction was completed. Then the solvent was completely removed under reduced pressure. The liquid remained was distilled under reduced pressure (boiling point: 85° C.@0.1 mmHg) and 29.5 g of the subject compound was obtained as a yellow liquid in 92% yield.

$^1$H NMR (C$_6$D$_6$): δ 5.96 (t, 2H, C$_5$H$_4$CH$_2$CH$_2$NCH$_3$), 5.79 (t, 2H, C$_5$H$_4$CH$_2$CH$_2$NCH$_3$), 3.68 (t, 2H, C$_5$H$_4$CH$_2$CH$_2$NCH$_3$), 3.08 (s, 3H, C$_5$H$_4$CH$_2$CH$_2$NCH$_3$), 2.93 (s, 12H, 2×N(CH$_3$)$_2$), 2.69 (t, 2H, C$_5$H$_4$CH$_2$CH$_2$NCH$_3$)

$^{13}$C NMR (C$_6$D$_6$): δ 136.51, 112.41, 106.92 (C$_5$H$_4$CH$_2$CH$_2$NCH$_3$), 71.53 (C$_5$H$_4$CH$_2$CH$_2$NCH$_3$), 43.98 N(CH$_3$)$_2$), 41.52 (C$_5$H$_4$CH$_2$CH$_2$NCH$_3$), 29.51 (C$_5$H$_4$CH$_2$CH$_2$NCH$_3$)

Example 2

Synthesis of (CpCH$_2$CH$_2$NCH$_3$)Zr(NEtMe)$_2$

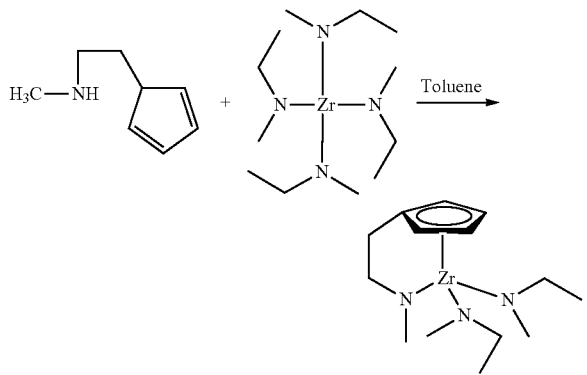

A 250 ml Schlenk flask was flame-dried and charged with 100 ml of toluene and 24.0 g (74.2 mmol; 1.00 equivalent) of tetrakis(ethylmethylamido) zirconium(IV). The mixture was stirred and cooled to −20° C. Then 10.0 g (81.2 mmol; 1.09 equivalents) of cyclopentadienylethylmethylamine synthesized in step-1 of example 1 was added over 30 minutes. After the solution was stirred at room temperature for 5 hours, the reaction was completed. Then the solvent was completely removed under reduced pressure. The liquid remained was distilled under reduced pressure (boiling point: 97° C.@0.1 mmHg) and 23 g of the subject compound was obtained as a yellow liquid in 89% yield.

$^1$H NMR (C$_6$D$_6$): δ 5.98 (m, 2H, C$_5$H$_4$CH$_2$CH$_2$NCH$_3$), 5.82 (m, 2H, C$_5$H$_4$CH$_2$CH$_2$NCH$_3$), 3.68 (t, 2H, C$_5$H$_4$CH$_2$CH$_2$NCH$_3$), 3.28~3.10 (m, 4H, 2×N(CH$_2$CH$_3$)(Me)), 3.07 (s, 3H, C$_5$H$_4$CH$_2$CH$_2$NCH$_3$), 2.98 (s, 6H, 2×N(CH$_3$)(Et)), 2.70 (t, 2H, C$_5$H$_4$CH$_2$CH$_2$NCH$_3$), 1.07 (t, 6H, 2×N(CH$_2$CH$_3$)(Me))

$^{13}$C NMR (C$_6$D$_6$): δ 136.25, 112.14, 106.65 (C$_5$H$_4$CH$_2$CH$_2$NCH$_3$), 71.51 (C$_5$H$_4$CH$_2$ CH$_2$NCH$_3$), 50.17 (N(CH$_3$)(Et)), 41.97 (N(CH$_2$CH$_3$)(Me)), 39.30 (C$_5$H$_4$CH$_2$CH$_2$N CH$_3$), 29.57 (C$_5$H$_4$CH$_2$CH$_2$NCH$_3$), 15.93 (N(CH$_2$CH$_3$)(Me)).

Example 3

Synthesis of (CpCH$_2$CH$_2$NCH$_3$)Zr(NEt$_2$)$_2$

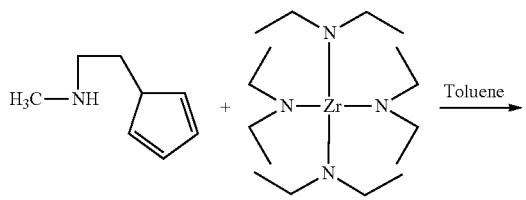

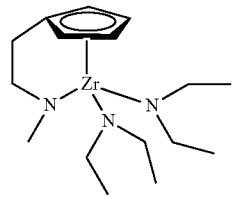

A 250 ml Schlenk flask was flame-dried and charged with 100 ml of toluene and 38.0 g (0.1 mol; 1.00 equivalent) of tetrakis(diethylamido) zirconium(IV). The mixture was stirred and cooled to −20° C. Then 13.5 g (0.11 mol; 1.10 equivalent) of cyclopentadienylethylmethylamine synthesized in step-1 of example 1 was added over 30 minutes. After reaction mixture was stirred at room temperature for 12 hours, the reaction was completed. Then the solvent was completely removed under reduced pressure. The liquid remained was distilled under reduced pressure (boiling point: 140° C.@0.1 mmHg) and 18 g of the subject compound was obtained as a yellow solid in 50% yield.

$^1$H NMR (C$_6$D$_6$): δ 5.98 (m, 2H, C$_5$H$_4$CH$_2$CH$_2$NCH$_3$), 5.84 (m, 2H, C$_5$H$_4$CH$_2$CH$_2$NCH$_3$), 3.68 (t, 2H, C$_5$H$_4$CH$_2$CH$_2$NCH$_3$), 3.24~3.12 (m, 8H, 4×N(CH$_2$CH$_3$)$_2$), 3.04 (s, 3H, C$_5$H$_4$CH$_2$CH$_2$NCH$_3$), 2.70 (t, 2H, C$_5$H$_4$CH$_2$CH$_2$NCH$_3$), 1.03 (t, 12H, 4×N(CH$_2$CH$_3$)$_2$)

$^{13}$C NMR (C$_6$D$_6$): δ 135.95, 112.92, 106.41 (C$_5$H$_4$CH$_2$CH$_2$NCH$_3$), 71.52 (C$_5$H$_4$CH$_2$CH$_2$NCH$_3$), 44.31 (N(CH$_2$CH$_3$)$_2$), 42.64 (C$_5$H$_4$CH$_2$CH$_2$NCH$_3$), 29.64 (C$_5$H$_4$CH$_2$CH$_2$NCH$_3$), 16.38 (N(CH$_2$CH$_3$)$_2$)

Example 4

Synthesis of (CpCH$_2$CH$_2$NCH$_3$)Zr(NEtMe)$_2$

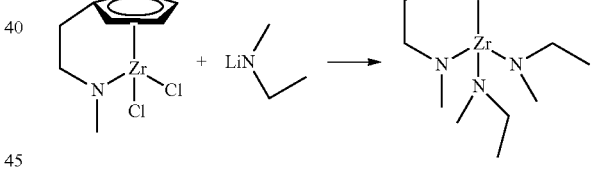

A 1 liter Schlenk flask was flame-dried and charged with 150 ml of toluene and 20.0 g (65.9 mmol; 1.00 equivalent) of cyclopentadienyl(ethylmethylamido) zirconium(IV) dichloride. The mixture was stirred and cooled to −20° C. To the mixture, 8.57 g (131.8 mmol; 2.00 equivalents) of lithium ethylmethylamide(LiNEtMe) suspended in 350 ml of n-hexane was added drop wise over 2 hours through a canula and the reaction mixture was stirred at room temperature for 15 hours. After allowing standing at room temperature for 5 hours, the supernatant was transferred to a flame-dried 1 liter Schlenk flask through a canula. Then the solvent was completely removed under reduced pressure. The liquid remained was distilled under reduced pressure (boiling point: 97° C.@0.1 mmHg) and 12.9 g of the subject compound was obtained as a yellow liquid in 50% yield.

$^1$H NMR (C$_6$D$_6$): δ 5.98 (m, 2H, C$_5$H$_4$CH$_2$CH$_2$NCH$_3$), 5.82 (m, 2H, C$_5$H$_4$CH$_2$CH$_2$NCH$_3$), 3.68 (t, 2H, C$_5$H$_4$CH$_2$CH$_2$NCH$_3$), 3.28~3.10 (m, 4H, 2×N(CH$_2$CH$_3$)(Me)), 3.07 (s, 3H, C$_5$H$_4$CH$_2$CH$_2$NCH$_3$), 2.98 (s, 6H, 2×N(CH$_3$)(Et)), 2.70 (t, 2H, C$_5$H$_4$CH$_2$CH$_2$NCH$_3$), 1.07 (t, 6H, 2×N(CH$_2$CH$_3$)(Me))

$^{13}$C NMR (C$_6$D$_6$): δ 136.25, 112.14, 106.65 (C$_5$H$_4$CH$_2$CH$_2$NCH$_3$), 71.51 (C$_5$H$_4$CH$_2$CH$_2$NCH$_3$), 50.17 (N(CH$_3$)(Et)), 41.97 (N(CH$_2$CH$_3$)(Me)), 39.30 (C$_5$H$_4$CH$_2$CH$_2$NCH$_3$), 29.57 (C$_5$H$_4$CH$_2$CH$_2$NCH$_3$), 15.93 (N(CH$_2$CH$_3$)(Me))

Example 5

Synthesis of (CpCH$_2$CH$_2$NCH$_3$)Ti(NMe$_2$)$_2$

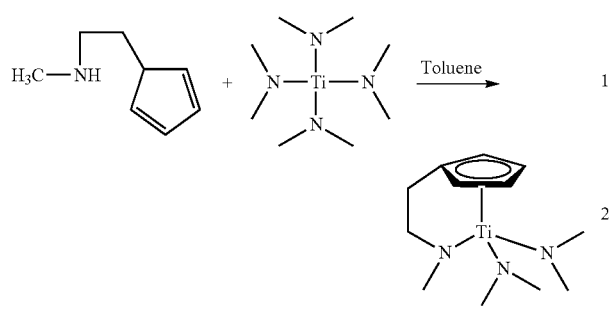

A 250 ml Schlenk flask was flame-dried and charged with 80 ml of toluene and 25.7 g (0.100 mol; 1.00 equivalent) of tetrakis(dimethylamido) Titanium(IV). The reaction mixture was stirred and cooled to −20° C. To the mixture, 12.3 g (0.10 mol; 1.00 equivalent) of cyclopentadienylethylmethylamine synthesized in step-1 of example 1 was added over 30 minutes. After mixture was stirred at room temperature for 1 hour, the reaction was completed. Then the solvent was completely removed under reduced pressure. The liquid remained was distilled under reduced pressure (boiling point: 80° C.@0.1 mmHg) and 18.0 g of the subject compound was obtained as a yellow liquid in 70% yield.

$^1$H NMR (C$_6$D$_6$): δ 5.81 (t, 2H, C$_5$H$_4$CH$_2$CH$_2$NCH$_3$), 5.70 (t, 2H, C$_5$H$_4$CH$_2$CH$_2$NCH$_3$), 3.66 (t, 2H, C$_5$H$_4$CH$_2$CH$_2$NCH$_3$), 3.34 (s, 3H, C$_5$H$_4$CH$_2$CH$_2$NCH$_3$), 3.07 (s, 12H, 2×N(CH$_3$)$_2$), 2.66 (t, 2H, C$_5$H$_4$CH$_2$CH$_2$NCH$_3$)

$^{13}$C NMR (C$_6$D$_6$): δ 136.01, 111.90, 108.15 (C$_5$H$_4$CH$_2$CH$_2$NCH$_3$), 73.24 (C$_5$H$_4$CH$_2$CH$_2$NCH$_3$), 48.33 (N(CH$_3$)$_2$), 46.19 (C$_5$H$_4$CH$_2$CH$_2$NCH$_3$), 29.22 (C$_5$H$_4$CH$_2$CH$_2$NCH$_3$)

Example 6

Synthesis of (CpCH$_2$CH$_2$NCH$_3$)Hf(NMe$_2$)$_2$

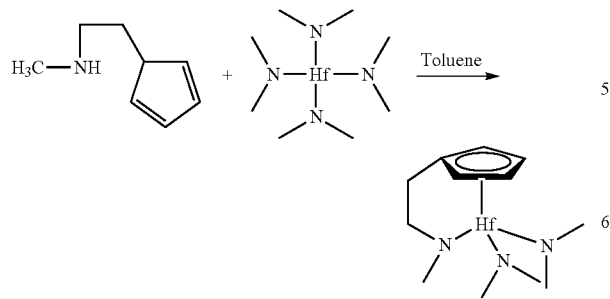

A 250 ml Schlenk flask was flame-dried and charged with 80 ml of toluene and 38.8 g (0.100 mol; 1.00 equivalent) of tetrakis(dimethylamido) Hafnium(IV). The reaction mixture was stirred and cooled to −20° C. To the reaction mixture, 12.3 g (0.10 mol; 1.00 equivalents) of cyclopentadienylethylmethylamine synthesized in step-1 of example 1 was added over 30 minutes. After mixture was stirred at room temperature for 2 hours, the reaction was completed. Then the solvent was completely removed under reduced pressure. The liquid remained was distilled under reduced pressure (boiling point: 90° C.@0.1 mmHg) and 31.0 g of the subject compound was obtained as a yellow liquid in 80% yield.

$^1$H NMR (C$_6$D$_6$): δ 5.92 (t, 2H, C$_5$H$_4$CH$_2$CH$_2$NCH$_3$), 5.76 (t, 2H, C$_5$H$_4$CH$_2$CH$_2$NCH$_3$), 3.80 (t, 2H, C$_5$H$_4$CH$_2$CH$_2$NCH$_3$), 3.06 (s, 3H, C$_5$H$_4$CH$_2$CH$_2$NCH$_3$), 2.96 (s, 12H, 2×N(CH$_3$)$_2$), 2.65 (t, 2H, C$_5$H$_4$CH$_2$CH$_2$NCH$_3$)

$^{13}$C NMR (C$_6$D$_6$): δ 135.03, 112.27, 106.48 (C$_5$H$_4$CH$_2$CH$_2$NCH$_3$), 71.31 (C$_5$H$_4$CH$_2$CH$_2$NCH$_3$), 43.83 (N(CH$_3$)$_2$), 41.59 (C$_5$H$_4$CH$_2$CH$_2$NCH$_3$), 29.12 (C$_5$H$_4$CH$_2$CH$_2$NCH$_3$)

Example 7

Synthesis of (CpCH$_2$CH$_2$NCH$_3$)Hf(NEtMe)$_2$

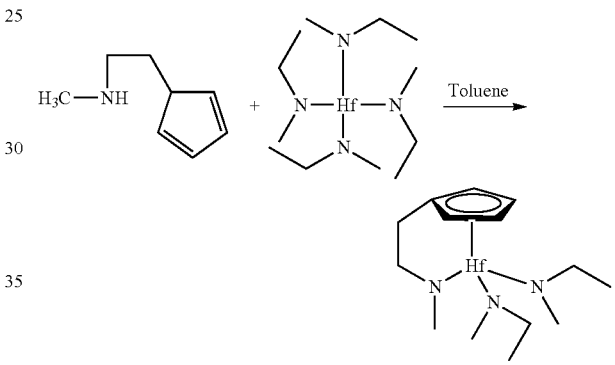

A 250 ml Schlenk flask was flame-dried and charged with 100 ml of toluene and 30.0 g (72.1 mmol; 1.00 equivalent) of tetrakis(ethylmethylamido) Hafnium(IV). The reaction mixture was stirred and cooled to −20° C. To the mixture, 10.0 g (81.2 mmol; 1.09 equivalents) of cyclopentadienylethylmethylamine synthesized in step-1 of example 1 was added over 30 minutes. After the reaction mixture was stirred at room temperature for 8 hours, the reaction was completed. Then the solvent was completely removed under reduced pressure. The liquid remained was distilled under reduced pressure (boiling point: 100° C.@0.1 mmHg) and 18 g of the subject compound was obtained as a yellow liquid in 60% yield.

$^1$H NMR (C$_6$D$_6$): δ 5.94 (m, 2H, C$_5$H$_4$CH$_2$CH$_2$NCH$_3$), 5.78 (m, 2H, C$_5$H$_4$CH$_2$CH$_2$NCH$_3$), 3.80 (t, 2H, C$_5$H$_4$CH$_2$CH$_2$NCH$_3$), 3.29~3.13 (m, 4H, 2×N(CH$_2$CH$_3$)(Me)); 3.05 (s, 3H, C$_5$H$_4$CH$_2$CH$_2$N CH$_3$), 2.93 (s, 6H, 2×N(CH$_3$)(Et)), 2.67 (t, 2H, C$_5$H$_4$ CH$_2$CH$_2$NCH$_3$), 1.06 (t, 6H, 2×N(CH$_2$CH$_3$)(Me))

Example 8

Thermal Stability Test of Zirconium Compounds

In these tests, both CpTDMAZ [cyclopentadienylzirconium(IV)tris(dimethylamide)] and cyclopentadienylethylmethylamidozirconium(IV)di(dimethylamide) synthesized in example 1 were used. After 10 g of test compound was introduced into each 20 ml glass bottle, the bottles were sealed with stoppers and further sealed by winding adhesive tape on the stopper. Then the bottles were introduced into glove boxes being under inert argon atmospheres. The two bottles containing above testing compounds were allowed to stand in oil bath for 6 hours at 110° C. and further for 2 hours at 150° C., and then cooled to room temperature.

The degree of thermal decomposition for above test compounds were determined by $^1$H nuclear magnetic resonance ($^1$H NMR) and the results were depicted in FIGS. 4A, 4B, 5A and 5B.

Figure 4A:
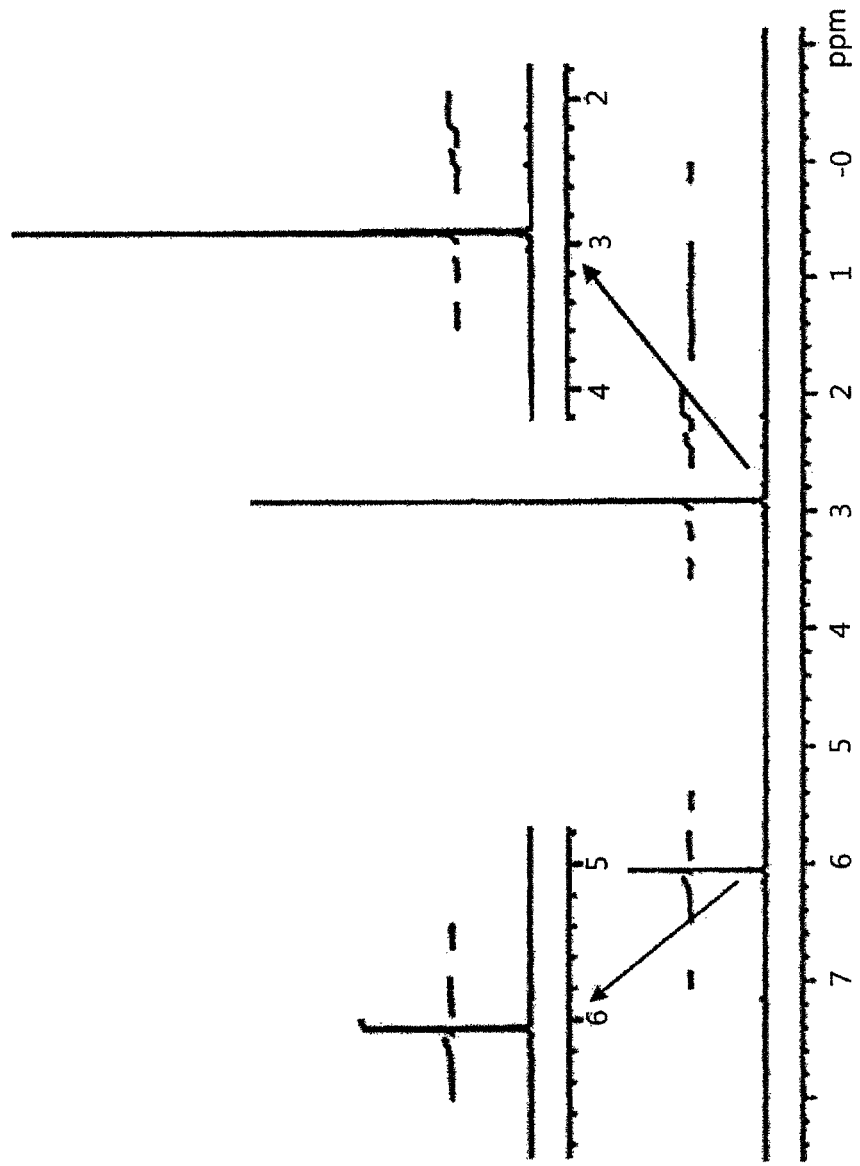
FIG. 4A is $^1$H nuclear magnetic resonance ($^1$H NMR) graph depicting state of CpTDMAZ before heating in test example 8.
Figure 4B:
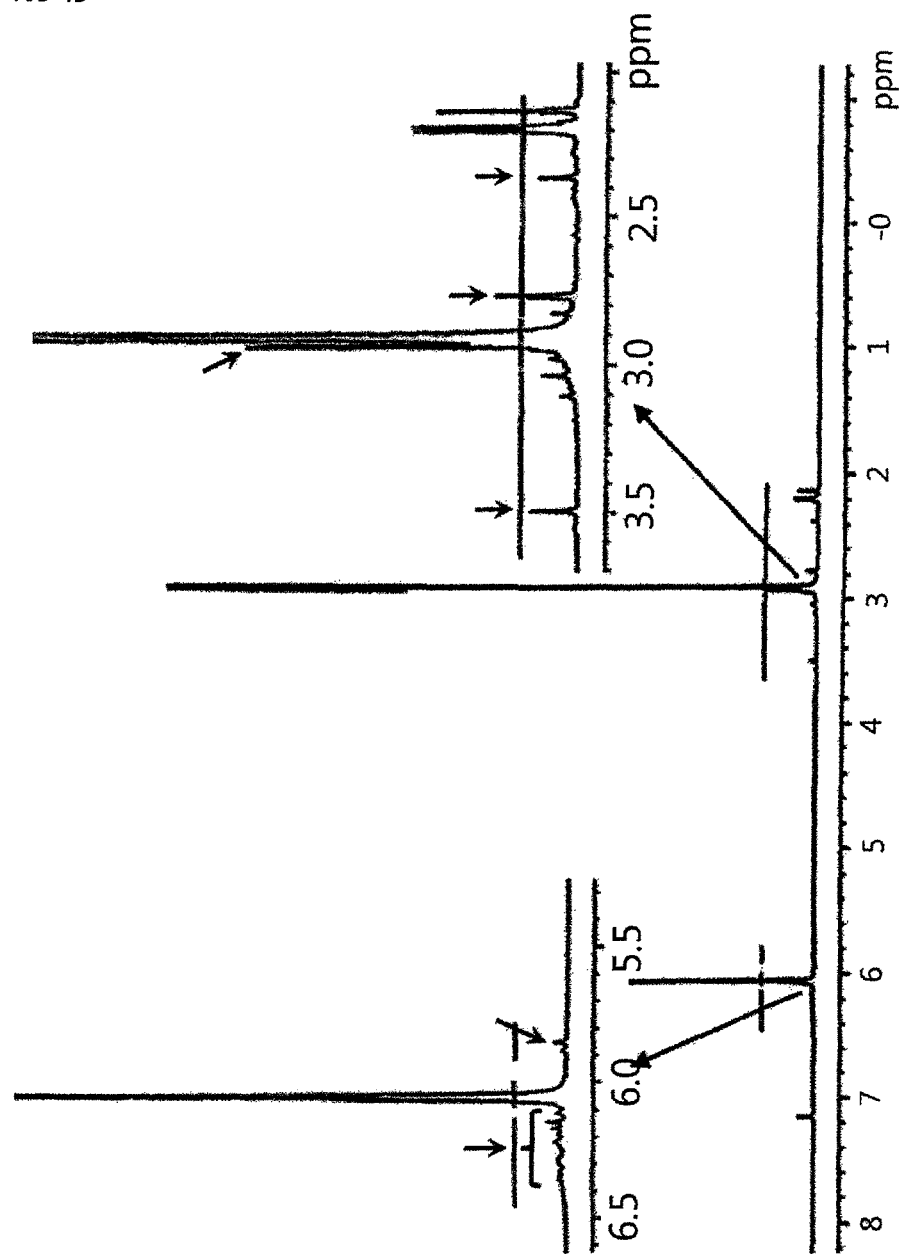
FIG. 4B is $^1$H NMR graph depicting state of CpTDMAZ after heating in test example 8.
Figure 5A:
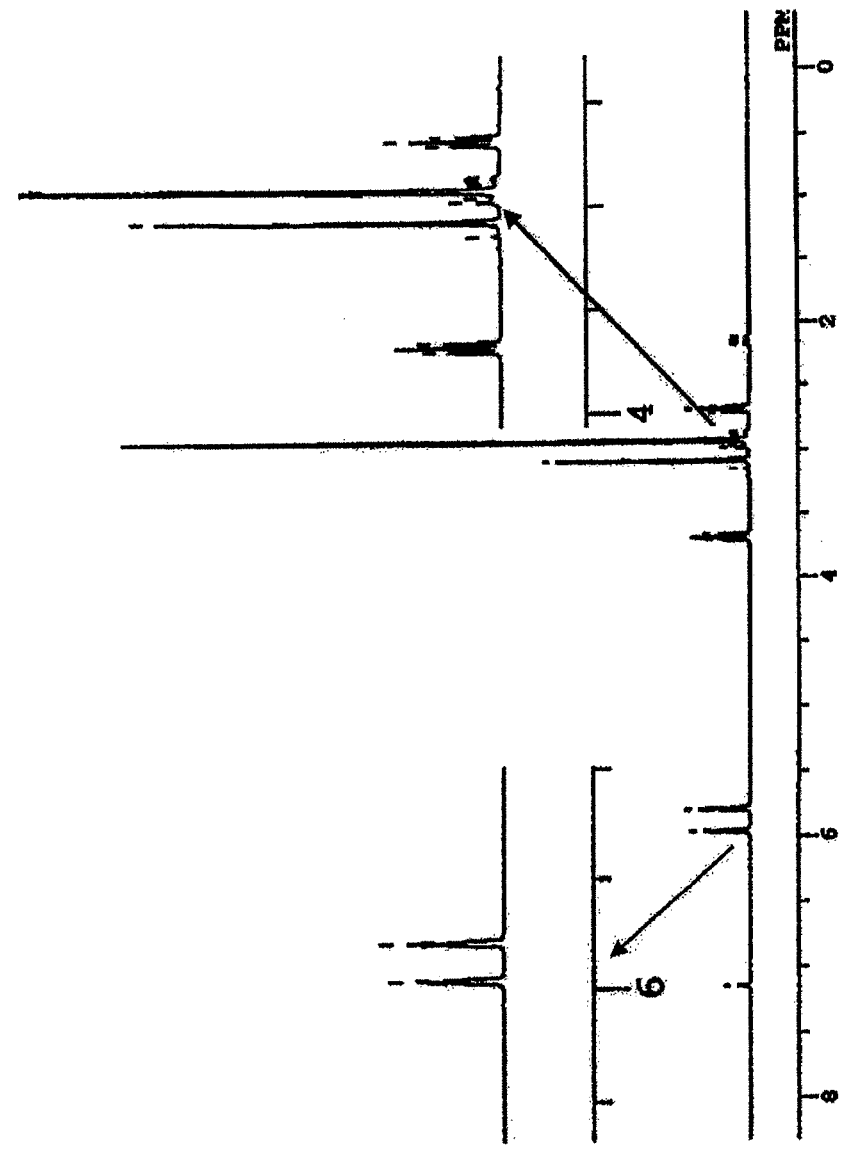
FIG. 5A is $^1$H NMR graph depicting state of compound (example 1) before heating in test example 8.
Figure 5B:
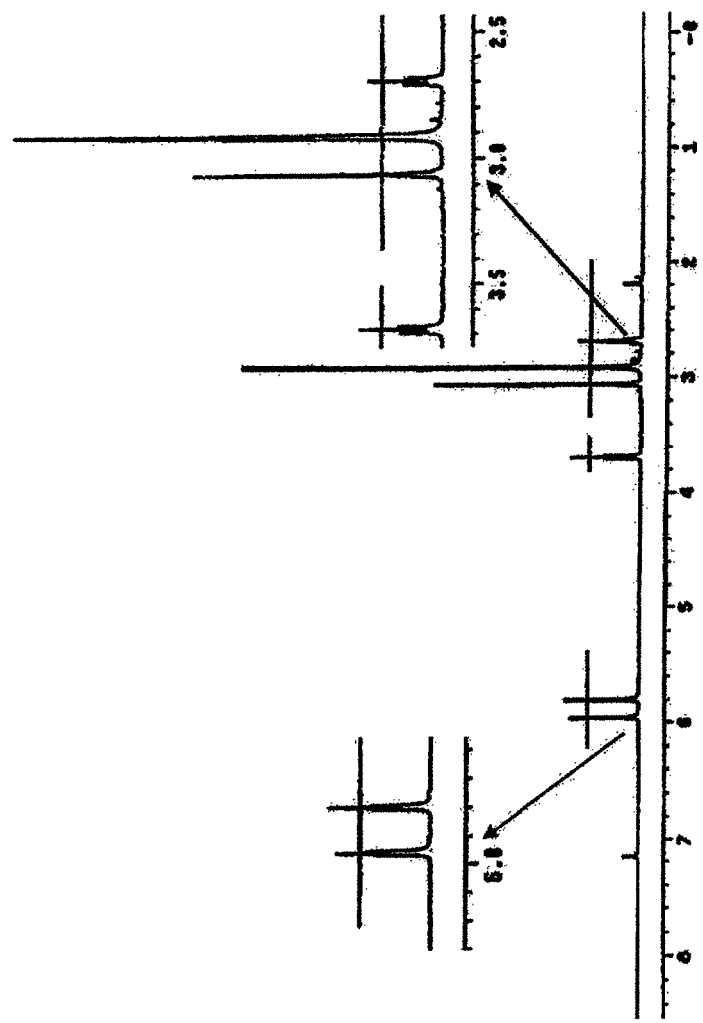
FIG. 5B is $^1$H NMR graph depicting state of compound (example 1) after heating in test example 8.

From $^1$H NMR graphs in FIGS. 4A and 4B, it was found that CpTDMAZ was easily decompose to produce impurities after heating. However, From $^1$H NMR graphs in FIGS. 5A and 5B, it was found that compound of example 1 has no specific change after heating.

Example 9

TGA Tests of Zr, Ti and Hf Compounds

Thermo-gravimetric-analysis (TGA) was performed for thermal stability tests. In these tests, TEMAZ [tetrakis-ethylmethylamidozirconium], CpTDMAZ [cyclopentadienylzirconium(IV)trisdimethylamide] and compounds synthesized in examples 1 and 2 were used. Above test compounds were heated to 400° C. at a rate of 10° C./minute under argon gas atmosphere introduced at a rate of 60 liters/minute. Temperatures ($T_{1/2}$° C.) at which weight of test compounds reduced to 50 wt % were determined. As listed in Table 1, $T_{1/2}$° C. of compounds synthesized in examples 1 and 2 were each 195° C. and 202° C., and $T_{1/2}$° C. of known TEMAZ and CpTDMAZ were each 164° C. and 176° C.

As a result, it confirms that $T_{1/2}$° C. of compounds in examples 1 and 2 are extremely higher than those of known TEMAZ and CpTDMAZ.

Thermal heat stability tests of TDMAT [Ti(NMe$_2$)$_4$; tetrakis-dimethylamidotitanium], TEMAH [Hf(NEtMe)$_4$; tetrakis-methylethylamidohafnium] and compounds synthesized in examples 5 and 7 were performed using same thermo-gravimetric-analysis (TGA). As listed in Table 2, $T_{1/2}$° C. of compound synthesized in examples 5 was 202° C., which is extremely higher than that of known TDMAT($T_{1/2}$° C.; 79° C.). Further, $T_{1/2}$° C. of compound synthesized in examples 7 was 181° C. which is 13° C. higher than that of known TEMAH ($T_{1/2}$° C.; 168° C.).

While the invention has been described herein with reference to various specific embodiments, it will be appreciated that the invention is not thus limited, and extends to and encompasses various modifications and embodiments, as will be appreciated by those ordinarily skilled in the art and will be broadly interpreted with the ensuing claims.

INDUSTRIAL APPLICABILITY

Novel metalorganic compounds comprising 4B group metals in the present invention have high thermal stability and high volatility, and can raise high efficiency and high reliability in a next generation semiconductor devices manufacturing processes.

What is claimed is:

1. A method of semiconductor element deposition comprising the step of depositing onto a substrate a 4B group metalorganic compound represented by Formula I:

(I)

[Structure of compound with cyclopentadienyl group bonded to M, with N-R$^1$, N-R$^2$, N-R$^2$R$^3$, R$^3$ substituents]

Wherein,
M represents Ti, Zr or Hf;
R$^1$ represents C$_1$~C$_4$ alkyl;
R$^2$ and R$^3$ represent independently C$_1$~C$_6$ alkyl.

2. The method of claim 1, wherein R$^1$, R$^2$ and R$^3$ represent independently methyl, ethyl or propyl.

3. The method of claim 2, wherein R$^1$, R$^2$ and R$^3$ represent independently methyl or ethyl.

4. The method of claim 3, wherein all of R$^1$, R$^2$ and R$^3$ represent methyl.

5. The method of claim 3, wherein both R$^1$ and R$^2$ represent methyl and R$^3$ represents ethyl.

6. The method of claim 1, wherein the compound is Zr(CpCH$_2$CH$_2$NMe)(NMe$_2$)$_2$, Zr(CpCH$_2$CH$_2$NMe)(NMeEt)$_2$, Zr(CpCH$_2$CH$_2$NMe)(NEt$_2$)$_2$, Zr(CpCH$_2$CH$_2$NMe)(NMe$^i$Pr)$_2$, Zr(CpCH$_2$CH$_2$NMe)(NEt$^i$Pr)$_2$, Zr(CpCH$_2$CH$_2$NMe)(N$^i$Pr$_2$)$_2$, Zr(CpCH$_2$CH$_2$NMe)(NMe$^n$Pr)$_2$, Zr(CpCH$_2$CH$_2$NMe)(NEt$^n$Pr)$_2$, Zr(CpCH$_2$CH$_2$NMe)(N$^n$Pr$_2$)$_2$, Zr(CpCH$_2$CH$_2$NEt)(NMe$_2$)$_2$, Zr(CpCH$_2$CH$_2$NEt)(NMeEt)$_2$, Zr(CpCH$_2$CH$_2$NEt)(NEt$_2$)$_2$, Zr(CpCH$_2$CH$_2$NEt)(NMe$^i$Pr)$_2$, Zr(CpCH$_2$CH$_2$NEt)(NEt$^i$Pr)$_2$, Zr(CpCH$_2$CH$_2$NEt)(N$^i$Pr$_2$)$_2$, Zr(CpCH$_2$CH$_2$NEt)(NMe$^n$Pr)$_2$, Zr(CpCH$_2$CH$_2$NEt)(NEt$^n$Pr)$_2$, Zr(CpCH$_2$CH$_2$NEt)(N$^n$Pr$_2$)$_2$, Zr(CpCH$_2$CH$_2$N$^i$Pr)(NMe$_2$)$_2$, Zr(CpCH$_2$CH$_2$N$^i$Pr)(NMeEt)$_2$, Zr(CpCH$_2$CH$_2$N$^i$Pr)(NEt$_2$)$_2$, Zr(CpCH$_2$CH$_2$N$^i$Pr)(NMe$^i$Pr)$_2$, Zr(CpCH$_2$CH$_2$N$^i$Pr)(NEt$^i$Pr)$_2$, Zr(CpCH$_2$CH$_2$N$^i$Pr)(N$^i$Pr$_2$)$_2$, Zr(CpCH$_2$CH$_2$N$^i$Pr)(NMe$^n$Pr)$_2$, Zr(CpCH$_2$CH$_2$N$^i$Pr)(NEt$^n$Pr)$_2$, Zr(CpCH$_2$CH$_2$N$^i$Pr)(N$^n$Pr$_2$)$_2$, Zr(CpCH$_2$CH$_2$N$^n$Pr)(NMe$_2$)$_2$, Zr(CpCH$_2$CH$_2$N$^n$Pr)(NMeEt)$_2$, Zr(CpCH$_2$CH$_2$N$^n$Pr)(NEt$_2$)$_2$, Zr(CpCH$_2$CH$_2$N$^n$Pr)(NMe$^i$Pr)$_2$, Zr(CpCH$_2$CH$_2$N$^n$Pr)(NEt$^i$Pr)$_2$, Zr(CpCH$_2$CH$_2$N$^n$Pr)(N$^i$Pr$_2$)$_2$, Zr(CpCH$_2$CH$_2$N$^n$Pr)(NMe$^n$Pr)$_2$, Zr(CpCH$_2$CH$_2$N$^n$Pr)(NEt$^n$Pr)$_2$, Zr(CpCH$_2$CH$_2$N$^n$Pr)(N$^n$Pr$_2$)$_2$, Ti(CpCH$_2$CH$_2$NMe)(NMe$_2$)$_2$, Ti(CpCH$_2$CH$_2$NMe)(NMeEt)$_2$, Ti(CpCH$_2$CH$_2$NMe)(NEt$_2$)$_2$, Ti(CpCH$_2$CH$_2$NMe)(NMe$^i$Pr)$_2$, Ti(CpCH$_2$CH$_2$NMe)(NEt$^i$Pr)$_2$, Ti(CpCH$_2$CH$_2$NMe)(N$^i$Pr$_2$)$_2$, Ti(CpCH$_2$CH$_2$NMe)(NMe$^n$Pr)$_2$, Ti(CpCH$_2$CH$_2$NMe)(NEt$^n$Pr)$_2$, Ti(CpCH$_2$CH$_2$NMe)(N$^n$Pr$_2$)$_2$, Ti(CpCH$_2$CH$_2$NEt)(NMe$_2$)$_2$, Ti(CpCH$_2$CH$_2$NEt)(NMeEt)$_2$, Ti(CpCH$_2$CH$_2$NEt)(NEt$_2$)$_2$, Ti(CpCH$_2$CH$_2$NEt)(NMe$^i$Pr)$_2$, Ti(CpCH$_2$CH$_2$NEt)(NEt$^i$Pr)$_2$, Ti(CpCH$_2$CH$_2$NEt)(N$^i$Pr$_2$)$_2$, Ti(CpCH$_2$CH$_2$NEt)(NMe$^n$Pr)$_2$, Ti(CpCH$_2$CH$_2$NEt)(NEt$^n$Pr)$_2$, Ti(CpCH$_2$CH$_2$NEt)(N$^n$Pr$_2$)$_2$, Ti(CpCH$_2$CH$_2$N$^i$Pr)(NMe$_2$)$_2$, Ti(CpCH$_2$CH$_2$N$^i$Pr)(NMeEt)$_2$, Ti(CpCH$_2$CH$_2$N$^i$Pr)(NEt$_2$)$_2$, Ti(CpCH$_2$CH$_2$N$^i$Pr)(NMe$^i$Pr)$_2$, Ti(CpCH$_2$CH$_2$N$^i$Pr)(NEt$^i$Pr)$_2$, Ti(CpCH$_2$CH$_2$N$^i$Pr)(N$^i$Pr$_2$)$_2$, Ti(CpCH$_2$CH$_2$N$^i$Pr)(NMe$^n$Pr)$_2$, Ti(CpCH$_2$CH$_2$N$^i$Pr)(NEt$^n$Pr)$_2$, Ti(CpCH$_2$CH$_2$N$^i$Pr)(N$^n$Pr$_2$)$_2$, Ti(CpCH$_2$CH$_2$N$^n$Pr)(NMe$_2$)$_2$, Ti(CpCH$_2$CH$_2$N$^n$Pr)(NMeEt)$_2$, Ti(CpCH$_2$CH$_2$N$^n$Pr)(NEt$_2$)$_2$, Ti(CpCH$_2$CH$_2$N"Pr)(NMe$^i$Pr)$_2$, Ti(CpCH$_2$CH$_2$N"Pr)(NEt$^i$Pr)$_2$, Ti(CpCH$_2$CH$_2$N"Pr)(N$^i$Pr$_2$)$_2$, Ti(CpCH$_2$CH$_2$N"Pr)(NMe"Pr)$_2$, Ti(CpCH$_2$CH$_2$N"Pr)(NEt"Pr)$_2$, Ti(CpCH$_2$CH$_2$N"Pr)(N"Pr$_2$)$_2$, Hf(CpCH$_2$CH$_2$NMe)(NMe$_2$)$_2$, Hf(CpCH$_2$CH$_2$NMe)(NMeEt)$_2$, Hf(CpCH$_2$CH$_2$NMe)(NEt$_2$)$_2$, Hf(CpCH$_2$CH$_2$NMe)(NMe$^i$Pr)$_2$, Hf(CpCH$_2$CH$_2$NMe)(NEt$^i$Pr)$_2$, Hf(CpCH$_2$CH$_2$NMe)(N$^i$Pr$_2$)$_2$, Hf(CpCH$_2$CH$_2$NMe)(NMe"Pr)$_2$, Hf(CpCH$_2$CH$_2$NMe)(NEt"Pr)$_2$, Hf(CpCH$_2$CH$_2$NMe)(N"Pr$_2$)$_2$, Hf(CpCH$_2$CH$_2$NEt)(NMe$_2$)$_2$, Hf(CpCH$_2$CH$_2$NEt)(NMeEt)$_2$, Hf(CpCH$_2$CH$_2$NEt)(NEt$_2$)$_2$, Hf(CpCH$_2$CH$_2$NEt)(NMe$^i$Pr)$_2$, Hf(CpCH$_2$CH$_2$NEt)(NEt$^i$Pr)$_2$, Hf(CpCH$_2$CH$_2$NEt)(N$^i$Pr$_2$)$_2$, Hf(CpCH$_2$CH$_2$NEt)(NMe"Pr)$_2$, Hf(CpCH$_2$CH$_2$NEt)(NEt"Pr)$_2$, Hf(CpCH$_2$CH$_2$NEO(N"Pr$_2$)$_2$, Hf(CpCH$_2$CH$_2$N$^i$Pr)(NMe$_2$)$_2$, Hf(CpCH$_2$CH$_2$N$^i$Pr)(NMeEt)$_2$, Hf(CpCH$_2$CH$_2$N$^i$Pr)(NEt$_2$)$_2$, Hf(CpCH$_2$CH$_2$N$^i$Pr)(NMe$^i$Pr)$_2$, Hf(CpCH$_2$CH$_2$N$^i$Pr)(NEt$^i$Pr)$_2$, Hf(CpCH$_2$CH$_2$N$^i$Pr)(N$^i$Pr$_2$)$_2$, Hf(CpCH$_2$CH$_2$N$^i$Pr)(NMe"Pr)$_2$, Hf(CpCH$_2$CH$_2$N$^i$Pr)(NEt"Pr)$_2$, Hf(CpCH$_2$CH$_2$N$^i$Pr)(N"Pr$_2$)$_2$, Hf(CpCH$_2$CH$_2$N"Pr)(NMe$_2$)$_2$, Hf(CpCH$_2$CH$_2$N"Pr)(NMeEt)$_2$, Hf(CpCH$_2$CH$_2$N"Pr)(NEt$_2$)$_2$, Hf(CpCH$_2$CH$_2$N"Pr)(NMe$^i$Pr)$_2$, Hf(CpCH$_2$CH$_2$N"Pr)(NEt$^i$Pr)$_2$, Hf(CpCH$_2$CH$_2$N"Pr)(N$^i$Pr$_2$)$_2$, Hf(CpCH$_2$CH$_2$N"Pr)(NMe"Pr)$_2$, Hf(CpCH$_2$CH$_2$N"Pr)(NEt"Pr)$_2$ or Hf(CpCH$_2$CH$_2$N"Pr)(N"Pr$_2$)$_2$ and wherein $^i$Pr and "Pr each represents isopropyl and normal propyl.

7. A composition for semiconductor element deposition comprising of 0.1 wt %~99.9 wt % of a 4B group organometallic compound according to claim 1 and remainders of one or more organic compounds selected from the group of saturated or unsaturated hydrocarbons, ethers (including cyclic ethers), esters, alcohols, amines (including cyclic amines), sulfides (including cyclic sulfides), phosphines, beta-diketones and beta-ketoesters.

8. A process for preparing the 4B group metalorganic compound of the formula (I),

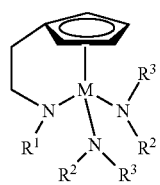

(I)

wherein M represents Ti, Zr or Hf, R$^1$ represents C$_1$~C$_4$ alkyl, R$^2$ and R$^3$ represent independently C$_1$~C$_6$ alkyl; characterized by reacting a compound of formula (IV)

M'NR$^2$R$^3$ (IV)

wherein R$^2$ and R$^3$ represent independently C$_1$~C$_6$ alkyl and M' represents Li, Na or K; with a metallic compound of formula (V)

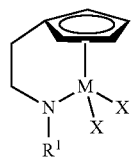

(V)

wherein M represents Ti, Zr or Hf, R$^1$ represents C$_1$~C$_4$ alkyl and X represents Cl, Br or I.

9. The process according to claim 8 for preparing the 4B group metalorganic compound of the formula I, characterized by using petroleum ether, hexane, pentane, heptane, diethyl ether, tetrahydrofuran, benzene, toluene or 1,2-dimethoxyethane as reaction solvent.

10. The method for forming a thin film containing a 4B group metal, comprising the steps of: vaporizing one or more metalorganic compound of the claim 1, and depositing it onto the silicon substrate or metal, ceramic, plastic structure.

11. The method according to claim 10 for forming a thin film, wherein the depositing step utilizes any one of heat energy, light energy or plasma, or bias voltage.

12. The method according to claim 11 for forming a thin film, wherein the depositing temperature is 100~1000° C.

13. The method according to claim 10 for forming a thin film, wherein the method of delivering the metalorganic compound onto substrate is one selected from float method, bubbling method, vapor phase mass flow controller (MFC) method, direct liquid injection (DLI) method or liquid transferring method using precursor compound-organic solvent solution.

14. The method according to claim 10 for forming a thin film, wherein the carrier gas or the dilution gas for delivering the metalorganic compound to substrate is any one selected from argon, nitrogen, helium, hydrogen, or a mixture thereof.

15. The method according to claim 10 for forming a thin film, wherein the thin film deposited on substrate is 4B group metal oxide(ZrO$_2$) film or metal oxides composite film thereof containing more than one film selected from the group of oxide film of Sc, Y, La, Ac, oxide film of Ti, Hf, oxide film of V, Nb, Ta, oxide film of AL, Ga, In, and oxide film of Si, Ge, Sn, Pb.

16. The method according to claim 10 for forming a thin film, wherein the thin film deposited on substrate is 4B group metal nitride (MN) film or metal nitrides composite film thereof containing more than one film selected from the group of nitride film of Sc, Y, La, Ac, nitride film of V, Nb, Ta, nitride film of AL, Ga, In, and nitride film of Si, Ge, Sn, Pb.

17. The method according to claim 10 for forming a thin film, wherein the thin film deposited on substrate is 4B group metal carbide (MC) film or metal carbide composite film thereof containing more than one film selected from the group of carbide film of Sc, Y, La, Ac, carbide film of V, Nb, Ta, carbide film of AL, Ga, In, and carbide film of Si, Ge, Sn, Pb.

18. The method according to claim 10 for forming a thin film, wherein the thin film deposited on substrate is 4B group metal carbon-nitride (MCN) film or metal carbon-nitride composite film thereof containing more than one film selected from the group of carbon-nitride film of Sc, Y, La, Ac, carbon-nitride film of V, Nb, Ta, carbon-nitride film of AL, Ga, In, and carbon-nitride film of Si, Ge, Sn, Pb.

19. The method according to claim 10 for forming a thin film, wherein the depositing procedure comprises the steps of;

(1) Carrying a substrate into reaction chamber and heating it to sintering temperature thereof;
(2) Introducing first purging gas into the reaction chamber (first purging step);
(3) Supplying a 4B group compound into the chamber to form an atomic layer on the substrate;
(4) Supplying a reaction gas into the chamber to react with the atomic layer; and
(5) Releasing off by-products and un-reacted materials of the 4B group compound from above chamber with second purging gas (second purging step).

* * * * *